(12) United States Patent
Dehe

(10) Patent No.: US 9,362,853 B2
(45) Date of Patent: Jun. 7, 2016

(54) PLATE, TRANSDUCER AND METHODS FOR MAKING AND OPERATING A TRANSDUCER

(71) Applicant: INFINEON TECHNOLOGIES AG, Neubiberg (DE)

(72) Inventor: Alfons Dehe, Reutlingen (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 13/902,462

(22) Filed: May 24, 2013

(65) Prior Publication Data

US 2013/0257218 A1      Oct. 3, 2013

Related U.S. Application Data

(62) Division of application No. 13/150,972, filed on Jun. 1, 2011, now Pat. No. 8,503,699.

(51) Int. Cl.
| | |
|---|---|
| *H02N 99/00* | (2006.01) |
| *H04R 7/10* | (2006.01) |
| *H04R 31/00* | (2006.01) |
| *G01N 21/956* | (2006.01) |
| *H01J 37/26* | (2006.01) |

(52) U.S. Cl.
CPC .............. *H02N 99/00* (2013.01); *G01N 21/956* (2013.01); *H01J 37/26* (2013.01); *H04R 7/10* (2013.01); *H04R 31/003* (2013.01); *Y10T 428/24281* (2015.01)

(58) Field of Classification Search
CPC ....... H02N 99/00; G01N 21/956; H01J 37/26; H04R 31/003; H04R 7/10; Y10T 428/24281
See application file for complete search history.

(56) References Cited

U.S. PATENT DOCUMENTS

| 3,573,399 A | 4/1971 | Schroeder et al. |
| 3,772,133 A | 11/1973 | Schmitt |
| RE28,420 E | 5/1975 | Murphy |
| 4,249,043 A | 2/1981 | Morgan et al. |

(Continued)

FOREIGN PATENT DOCUMENTS

| CN | 101222792 A | 7/2008 |
| CN | 101347040 A | 1/2009 |

(Continued)

OTHER PUBLICATIONS

4-Note Snail Design Log Drum, http://www.amazon.com/4-Note-Snail-Design-Log-Drum/dp/B0002KMTSE, downloaded for reference Apr. 22, 2015, 3 pages.

(Continued)

*Primary Examiner* — Laura Menz
(74) *Attorney, Agent, or Firm* — Slater Matsil, LLP

(57) ABSTRACT

A plate, a transducer, a method for making a transducer, and a method for operating a transducer are disclosed. An embodiment comprises a plate comprising a first material layer comprising a first stress, a second material layer arranged beneath the first material layer, the second material layer comprising a second stress, an opening arranged in the first material layer and the second material layer, and an extension extending into opening, wherein the extension comprises a portion of the first material layer and a portion of the second material layer, and wherein the extension is curved away from a top surface of the plate based on a difference in the first stress and the second stress.

24 Claims, 8 Drawing Sheets

(56) References Cited

U.S. PATENT DOCUMENTS

| | | | |
|---|---|---|---|
| 4,442,324 A | 4/1984 | Blanchard et al. | |
| 4,567,382 A | 1/1986 | van Halteren | |
| 4,982,647 A | 1/1991 | Hertzberg et al. | |
| 5,490,220 A | 2/1996 | Loeppert | |
| 5,870,482 A | 2/1999 | Loeppert et al. | |
| 6,647,766 B2 | 11/2003 | Despont et al. | |
| 6,775,388 B1 | 8/2004 | Pompei | |
| 6,862,925 B2 | 3/2005 | Desponet et al. | |
| 6,866,255 B2 | 3/2005 | Fork et al. | |
| 7,082,684 B2 | 8/2006 | Hantschel et al. | |
| 7,172,707 B2 | 2/2007 | Fork et al. | |
| 7,190,038 B2 | 3/2007 | Dehe et al. | |
| 7,253,016 B2 | 8/2007 | Barzen et al. | |
| 7,348,646 B2 | 3/2008 | Barzen et al. | |
| 7,372,348 B2 | 5/2008 | Xu et al. | |
| 7,473,572 B2 | 1/2009 | Dehe et al. | |
| 7,522,029 B1 | 4/2009 | Lantz | |
| RE40,781 E | 6/2009 | Johannsen et al. | |
| 7,545,252 B1 | 6/2009 | Lantz | |
| 7,687,108 B2 | 3/2010 | Xu et al. | |
| 7,898,048 B2 | 3/2011 | Nakatani | |
| 7,912,236 B2 * | 3/2011 | Dehe et al. | 381/175 |
| 7,961,897 B2 | 6/2011 | Weigold | |
| 8,265,309 B2 | 9/2012 | Zhang | |
| 8,358,793 B2 | 1/2013 | Weigold | |
| 2001/0038598 A1 | 11/2001 | Despont et al. | |
| 2004/0107770 A1 | 6/2004 | Despont et al. | |
| 2004/0259286 A1 | 12/2004 | Dehe et al. | |
| 2005/0002536 A1 | 1/2005 | Gorelik et al. | |
| 2005/0179100 A1 | 8/2005 | Barzen et al. | |
| 2006/0030066 A1 | 2/2006 | Hantschel et al. | |
| 2006/0038643 A1 | 2/2006 | Xu et al. | |
| 2006/0141656 A1 | 6/2006 | Dehe et al. | |
| 2006/0177083 A1 | 8/2006 | Sjursen et al. | |
| 2006/0228917 A1 | 10/2006 | Hantschel et al. | |
| 2007/0023851 A1 | 2/2007 | Hartzell et al. | |
| 2007/0034976 A1 | 2/2007 | Barzen et al. | |
| 2007/0201710 A1 | 8/2007 | Suzuki et al. | |
| 2008/0104825 A1 | 5/2008 | Dehe et al. | |
| 2008/0115586 A1 | 5/2008 | Low et al. | |
| 2008/0192962 A1 | 8/2008 | Halteren | |
| 2008/0247572 A1 * | 10/2008 | Langereis et al. | 381/174 |
| 2009/0169035 A1 | 7/2009 | Rombach et al. | |
| 2009/0303839 A1 | 12/2009 | Narayanan et al. | |
| 2009/0320992 A1 | 12/2009 | Xu et al. | |
| 2010/0096714 A1 | 4/2010 | Nakatani | |
| 2010/0285700 A1 | 11/2010 | Chow et al. | |
| 2011/0170735 A1 | 7/2011 | Dehe et al. | |
| 2011/0216922 A1 | 9/2011 | Li et al. | |
| 2011/0255716 A1 | 10/2011 | Ge et al. | |
| 2012/0148071 A1 | 6/2012 | Dehe | |
| 2012/0207332 A1 | 8/2012 | Dehe | |
| 2012/0248554 A1 | 10/2012 | Klein et al. | |
| 2012/0308053 A1 | 12/2012 | Dehe | |
| 2012/0328132 A1 | 12/2012 | Wang | |
| 2013/0056840 A1 | 3/2013 | Bominaar-Silkens et al. | |
| 2013/0062710 A1 | 3/2013 | Dehe | |
| 2014/0079277 A1 | 3/2014 | Dehe et al. | |

FOREIGN PATENT DOCUMENTS

| | | |
|---|---|---|
| CN | 101353151 A | 1/2009 |
| DE | 102006055147 A1 | 5/2008 |
| JP | 2006295245 A | 10/2006 |
| JP | 2007049473 A | 2/2007 |
| JP | 2011010132 A | 1/2011 |
| WO | WO03098969 A2 | 11/2003 |
| WO | 2007097520 A1 | 8/2007 |

OTHER PUBLICATIONS

Golden Bridge Log Drum, Sku #473078000000000, http://www.music123.com/classroom-kids/golden-bridge-log-drum, downloaded for reference Apr. 22, 2015, 1 page.

"Slit Drum," http//de.wikipedia.org/wiki/Schlitztrommel, downloaded for reference on Apr. 22, 2015, 4 pages.

* cited by examiner

PLATE, TRANSDUCER AND METHODS FOR MAKING AND OPERATING A TRANSDUCER

CROSS-REFERENCES TO RELATED APPLICATIONS

This is a divisional application of U.S. application Ser. No. 13/150,972, entitled "Plate, Transducer and Methods for Making and Operating a Transducer" which was filed on Jun. 1, 2011 and is incorporated herein by reference.

TECHNICAL FIELD

The present invention relates generally to a plate, a transducer and methods of making and operating a transducer.

BACKGROUND

Generally, a transducer is a device that converts one type of energy to another. The conversion can be to/from electrical, electro-mechanical, electromagnetic, photonic, photovoltaic, or any other form of energy. While the term transducer commonly implies use as a sensor/detector, any device which converts energy can be considered as a transducer.

SUMMARY OF THE INVENTION

In accordance with an embodiment of the present invention, a plate comprises a first material layer comprising a first stress and a second material layer arranged beneath the first material layer, the second material layer comprising a second stress. The plate further comprises an opening arranged in the first material layer and the second material layer and an extension shaping the opening, wherein the extension comprises a portion of the first material layer and a portion of the second material layer, and wherein the extension is curved away from a top surface of the plate based on a difference between the first stress and the second stress.

In accordance with an embodiment of the present invention, a transducer comprises a membrane, a back-plate comprising an opening, the opening comprising a convex portion, wherein the convex portion is curved toward the membrane, and a spacer between the membrane and the back-plate.

In accordance with an embodiment of the present invention, a method for operating a transducer comprises receiving a sound wave at a membrane, moving the membrane toward a back-plate, wherein the back-plate comprises an opening, wherein an extension extends into the opening, and wherein the extension is curved toward the membrane, and generating a signal in response to the moving membrane.

In accordance with an embodiment of the present invention, a method for manufacturing a transducer comprises forming a membrane in a substrate and forming a back-plate comprising a first material layer and a second material layer, the first material layer comprising a different stress than the second material layer. The method further comprises forming an opening in the back-plate, the opening comprising an extension extending into the opening, wherein forming the opening comprises etching the opening in the first material layer using a first etch process, and etching the opening in the second material layer using a second etch process.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to embodiments in a specific context, namely a membrane. The invention may also be applied, however, to other devices having a movable element and a fixed element, wherein the movable element moves relative to the fixed element.

Transducers may convert electrical, electro-mechanical, electromagnetic, photonic, photovoltaic energy to another type of energy. For example, a transducer can be a capacitor with a movable electrode. The movable electrode may move against a fixed electrode resulting in a change of capacity between the two electrodes. The change in capacity is provided to an output. The transducer is typically operated by a bias voltage, i.e. a potential which may be adjusted freely to the respective circumstances, that is applied between the membrane and the counter electrode.

The transducer may be a stand alone device or may be connected to a simple application specific integrated circuit (ASIC). Alternatively, the transducer may be integrated in an integrated circuit (IC).

One example of a transducer is a microphone. A microphone converts sound energy of a sound wave into electrical energy. The movable membrane or electrode may be mechanically connected to a substrate and has a volume of air surrounding it. Pressure changes of the sound waves deform or deflect the membrane. A back-plate or counter-electrode may comprise openings so that air between the back-plate and the membrane can freely displace and the movement of the membrane is not dampened.

A challenge in manufacturing and/or operating a microphone is that the movable membrane should not adhere or stick to the back-plate. To prevent that, conventional devices may have a coating layer on the movable membrane and/or the back-plate or arrange anti-sticking bumps on the back-plate to minimize or avoid stiction.

An advantage of an embodiment of the present invention is that stiction in the micro structure is prevented. Another advantage of an embodiment is that the contact area between the membrane and the back-plate is reduced. A further advantage of an embodiment is that the membrane is not pierced or damaged by bent extensions.

In one embodiment an extension is formed in an opening of the back-plate. The extension may be bent towards the movable membrane reducing the potential contact area between the movable membrane and the back-plate. The extension may be in its equilibrium position if not touched by the membrane and may be displaced from its equilibrium position if touched by the membrane.

Figure 1:
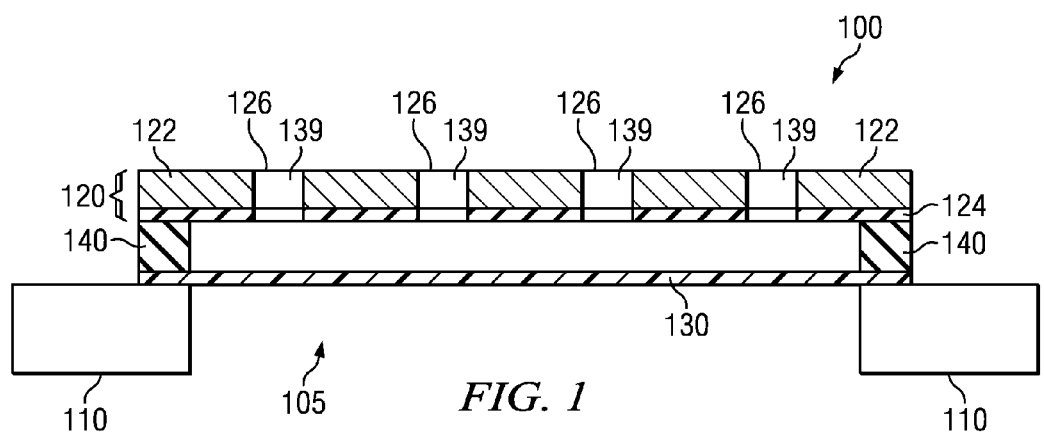
FIG. 1 illustrates a cross sectional view of a microphone.

FIG. 1 shows a microphone 100 arranged in or on a support substrate 110. The microphone 100 comprises a back-plate 120 and a membrane 130. The back-plate 120 is spaced apart from the membrane 130 by a spacer 140. The space between the back-plate 120 and the membrane 130 may be filled with free air, i.e. with air which does not dampen the movement of the membrane 130. The air is free because openings 139 at opening locations 126 in the back-plate 120 let the air exhaust if the membrane 130 moves towards the back-plate 120 and an opening 105 in the support substrate 110 let the air exhaust if the membrane 130 moves in the other direction, away from the back-plate 120. The back-plate 120 and the membrane 130 may be electrodes. While the back-plate 120 may be a fixed electrode, the membrane 130 may be a movable electrode.

The back-plate 120 may comprise a first material layer 122 and a second material layer 124. The first material layer 122 may be a conductive layer comprising doped polysilicon, a metal, or other conductive materials. The second material layer 124 may comprise an insulating material such as a nitride, an oxide or the like. Alternatively, the second material layer 124 may comprise a conductive material. The first material layer 122 may be relatively thick while the second material layer 124 may be relatively thin. For example, the first material layer 122 may be about 300 nm to about 3000 nm thick, and the second material layer 124 may be about 30 nm to about 300 nm thick.

The back-plate 120 may comprise a plurality of openings 139. Conventional back-plates may have perfectly round perforations. Embodiments of the invention provide openings which may not be perfectly round, which may comprise a convex portion and/or which may comprise one or more extensions shaping the openings. Layouts of embodiments of these openings are disclosed and discussed in FIGS. 2a-2b, 3a-3d and 4a-4e. In one embodiment a first opening of the back-plate may feature one type of opening while a second opening may feature another type of opening.

The plurality of the openings 139 and extensions 128 may be formed by a double lithography/etch process. In a first step the first material layer 122 may be structured and material may be removed where the openings are located and in a second step the second material layer 124 may be structured and material may be removed in order to finalize the openings. The extensions 128 may bend automatically when the openings are formed because of the bimorph character of the combination of the first and second material layers 122, 124, e.g., the difference in stress in the first and second material layers 122, 124.

The membrane 130 may be as thin as possible so that it will deform significantly with slight changes in pressure, e.g., small sound pressure levels. However, the thickness reduction of the membrane 130 may be limited because of stability requirements (destruction with too high a sound pressure or too high a voltage) and the requirement that stiction to the back-plate 120 should be prevented. In one example, the membrane 130 may be about 1 mm in diameter and about 3 μm thick.

The membrane 130 may comprise a conductive material such as doped or undoped polysilicon, or the like. The membrane 130 may be arranged to be movable relative to the back-plate 120. The membrane 130 may be mechanically connected along its circumference to the substrate 110 and may be electrically contacted to contact pads. The contact pads may be arranged on the substrate 110.

The spacer 140 may comprise an insulating material such as an oxide or a nitride. The spacer 140 may comprise a thickness of about 2 μm or less as an example. The substrate 110 may be a semiconductor substrate such as bulk silicon, SiGe or the like.

Figure 2A:
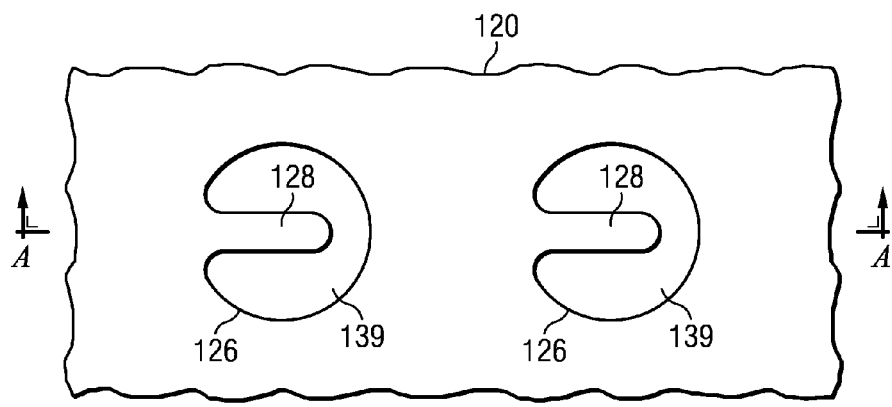
FIG. 2a illustrates a top view of an embodiment of an opening in the back-plate.
Figure 2B:
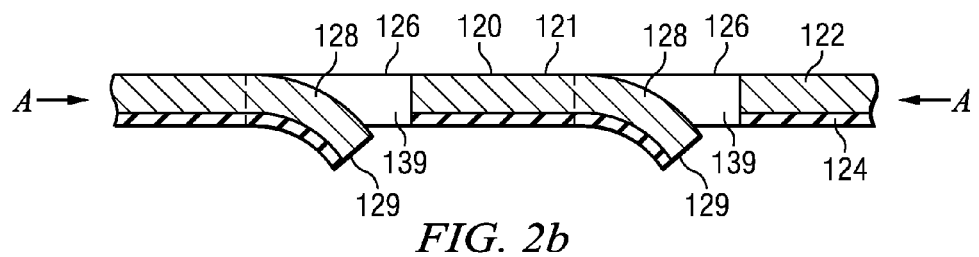
FIG. 2b illustrates a cross sectional view of the back-plate.

FIG. 2a shows a layout of an embodiment of the opening locations 126 in the back-plate 120. An extension 128 extends into the opening 139 shaping the opening 139. The extension 128 has the form of a cantilever or beam. FIG. 2b shows a cross-sectional view along the line A-A. As can be seen from FIG. 2b, the extension 128 is bent away in a direction normal to a top surface 121 of the back-plate 120.

In an embodiment the material of the first material layer 122 may comprise a different stress than the material of the second material layer 124. For example, the first material layer 122 may have a lower tensile stress than the second material layer 124. Alternatively, the first material layer 122 may have a higher compressive stress than the second material layer 124. The different stress material layers may cause the extension 128 to bend. The extension 128 may bend towards movable membrane 130.

Figure 2C:
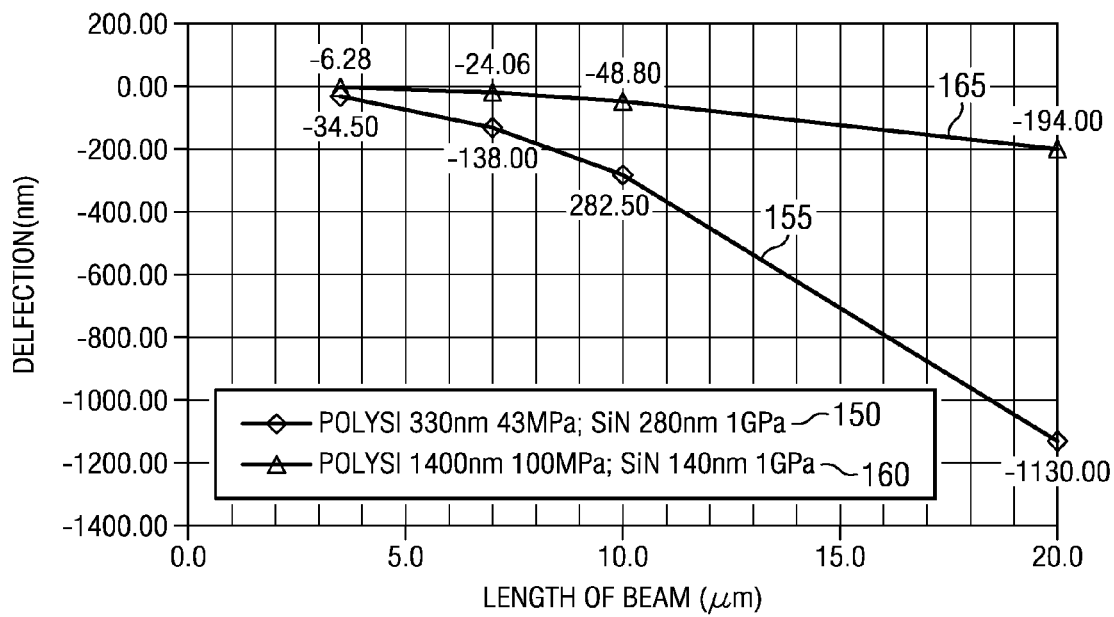
FIG. 2c illustrates a chart with graphs for different back-plate material compositions.
Figure 2D:
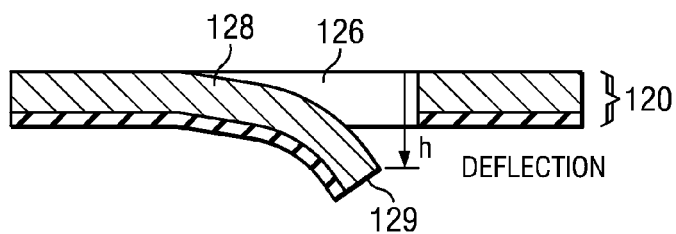
FIG. 2d illustrates the deflection of the extension relative to the back-plate.

FIG. 2c shows two different graphs 155/165 for two different material compositions 150/160 for the two material layers 122, 124. The two graphs 155/165 show bending relative to length of the extension 128. In a first material composition 150 the first material layer 122 is 330 nm thick, has a stress of 43 MPa, and comprises polysilicon, and the second material layer 124 is 280 nm thick, has a stress of 1 GPa and comprises silicon nitride. The first material composition 150 results in graph 155. As can be seen from this graph 155, the deflection h for the extension 128 shown in FIG. 2d is −1130 nm for a beam of 20 μm length. In a second material composition 160 the first material layer 122 is 1400 nm thick, has a stress of 100 MPa, and comprises polysilicon, and the second material layer 124 is 140 nm thick, has a stress of 1 GPa, and comprises silicon nitride. The first material composition 150 results in graph 165. As can be seen from this graph 165, the deflection h for extension 128 is −194 nm for a beam of 20 μm length.

The deflection or bending height h is the difference between the tip 129 of the extension 128 and the upper surface of the back-plate 120 as can be seen from FIG. 2d. The bending height h is controlled by the materials of the first and second material layers 122, 124, by the stress of these materials and/or by the length of the extension 128. As can be seen from FIG. 2c any deflection h can be designed by choosing the correct material composition, stress relations and extension length.

Figure 3A:
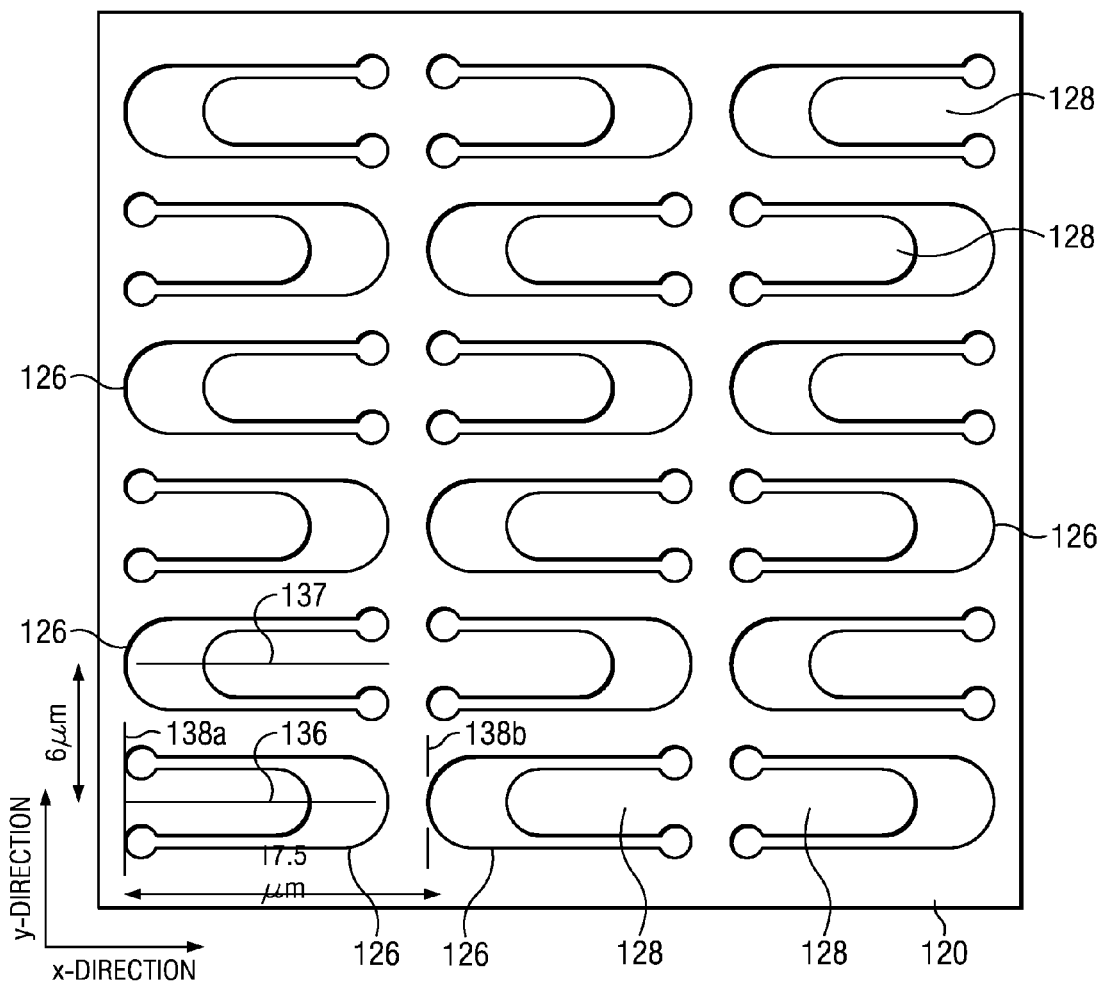
FIG. 3a illustrates an embodiment of a layout of a back-plate.

FIG. 3a shows an embodiment of a layout of a back-plate 120. The back-plate 120 comprises elongated opening locations 126 arranged alternately in x-direction and in y-direction. Each elongated opening location 126 comprises a beam or cantilever 128 extending into the elongated opening 139. A distance in y-direction from a first center line 136 of a first elongated opening location 126 to a second center line 137 of a second elongated opening location 126 is 6 μm. A distance in x-direction from a first end 138 of a first elongated opening location 126 to a first end 139 of a second elongated opening location 126 is 17.5 μm. The embodiment of FIG. 3*a* may allow an easy scaling of the elongated opening locations 126 and the cantilever 128. A desired deflection h may be defined by the length of the cantilever 128. The longer the cantilever 128 the higher may be the deflection h. For example, a low air damping may be achieved when a deflection h of the cantilever 128 is wider than the thickness of the back-plate 120. Such an arrangement may be used for microphones 100 in high sensitivity applications or in high signal to noise ratios applications.

Figure 3B:
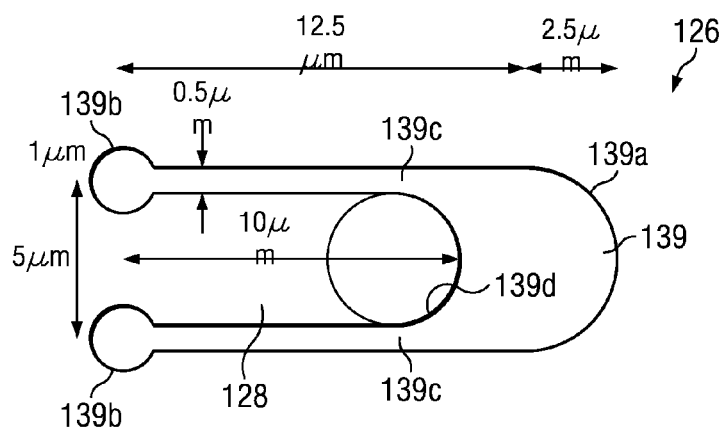
FIG. 3b illustrates a top view of an embodiment of an elongated opening.

FIG. 3*b* shows a top view of an elongated opening location 126 having a beam 128 forming the opening 139. In this example, the beam 128 is 10 μm long and 5 μm wide. The elongated opening location 126 may be 15 μm long and 6 μm wide. As can be seen from FIG. 3*b* the elongated opening location 126 has an opening 139. The area of the extension 128 and the area of the opening 139 together form the area of the opening location 126. The plurality of openings 139 generates an effective open area of 26% when placed in the back-plate 120 as shown in FIG. 3*a*. The effective open area is a parameter when calculating the damping of air flowing through these openings 139. The opening 139 comprises a concave portion 139*a* having a radius of 2.5 μm and a convex portion 139*d*. The opening 139 also comprises two holes 139*b* having a diameter of 1 μm. The two holes 139*b* are connected to the concave portion 139*a* via elongated gaps 139*c*, the gaps being 0.5 μm wide. The holes 139*b* at the end of the 0.5 μm slot may reduce the stress concentration in adjacent regions surrounding the holes 139*b*. Without the holes 139*b* there would be an increased notching effect.

Figure 3C:
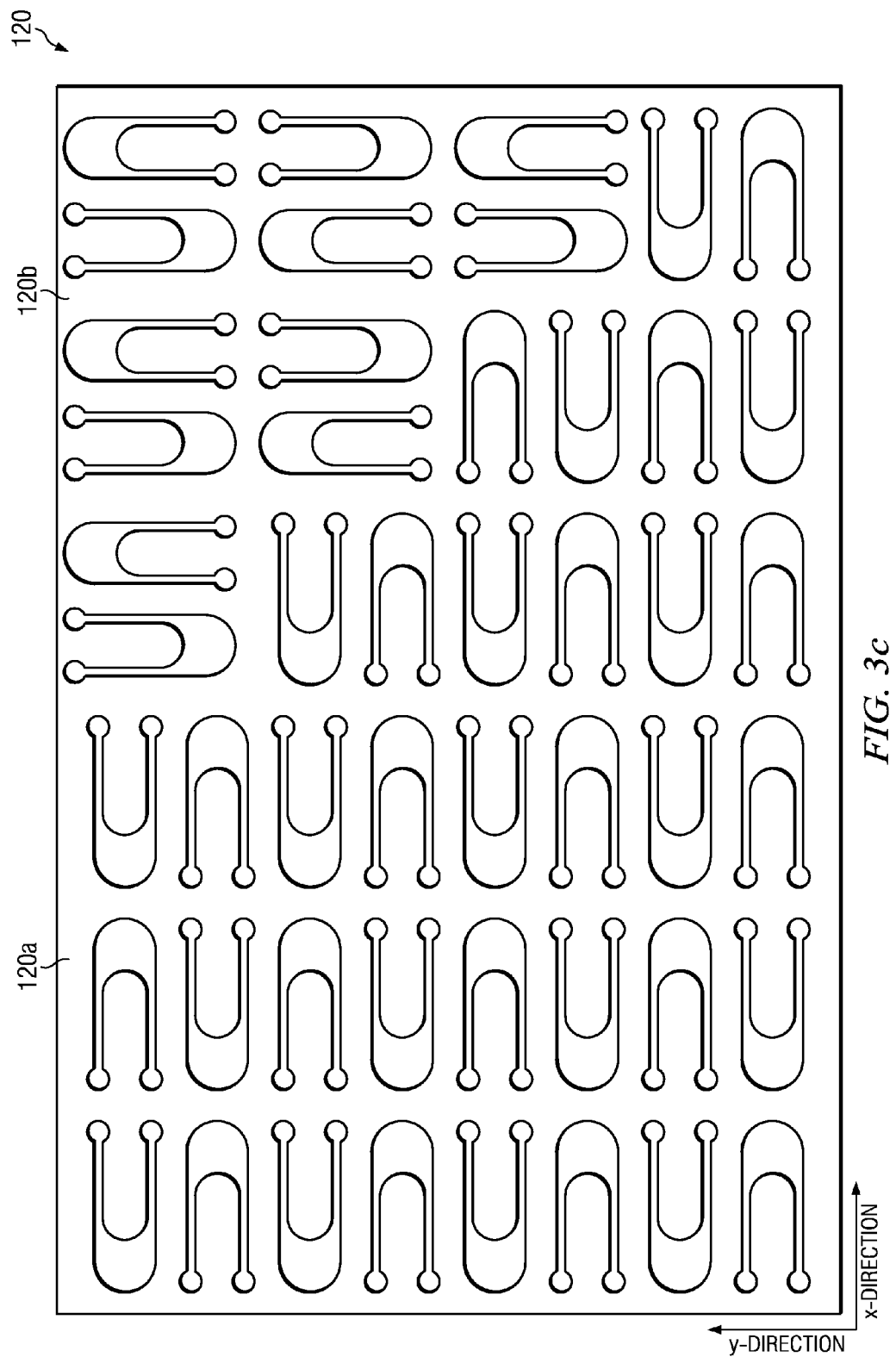
FIG. 3c illustrates an embodiment of a layout of a back-plate.

FIG. 3*c* shows another embodiment of a layout of the back-plate 120. The back-plate 120 comprises a first region 120*a* where a plurality of first elongated opening locations 126 is aligned in x-direction and a second region 120*b* where a plurality of elongated opening locations 126 is aligned in y-direction. The first region 120*a* may comprise at least 2 elongated opening locations 126 and the second region 120*b* may comprise at least 2 elongated opening locations 126.

The alignment of the extensions 128 in different directions may be advantageous in rotational symmetric microphone applications wherein the membrane 130 is round, for example. The membrane 130 typically shows a balloon type bowing when displaced extensively. In the event that the membrane 130 touches the back-plate 120 the curved cantilevers 128 in the middle of the back-plate 120 are touched first and the curved cantilevers 128 near the round edge are touched later. The curved beams 128 are arranged in radial direction so that in case of a contact between the membrane 130 and the curved beams 128 the beams 128 may experiences no or almost no movement perpendicular to its elongation.

Figure 3D:
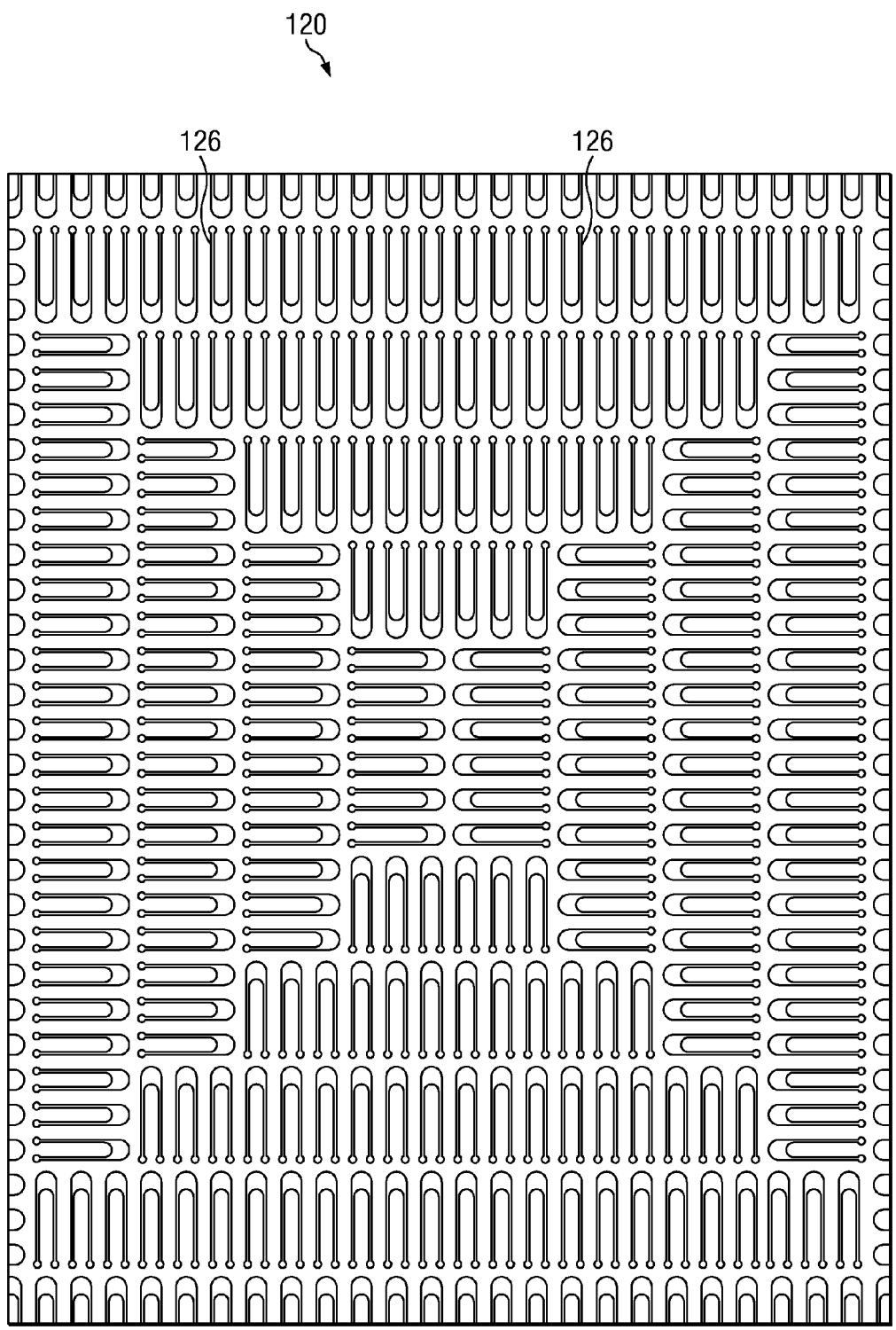
FIG. 3d illustrates an embodiment of a layout of a back-plate.

FIG. 3*d* shows another embodiment of a layout of the back-plate 120. The back-plate 120 comprises a symmetric arrangement of elongated opening locations 126. The elongated opening locations 126 are all facing toward a center point P. In this particular example, the combined distance of three neighboring elongated openings 126 (e.g., measured as the distance in y-direction of FIG. 3*a*) is the same as the length of one elongated opening 126.

FIG. 3*a*-3*d* show specific examples of how elongated opening locations 126 can be arranged in the back-plate 120. However, there are many other possible arrangements. For example, the elongated opening locations 126 may all be arranged facing in the same direction, e.g., the concave portions 139*a* of the openings 139 are arranged on the left side of the elongated opening locations 126. The elongated opening locations 126 of two rows may be parallel shifted or staggered relative to one other. In a further example, the elongated opening locations 126 may not be arranged in a preferred direction (x- or y-direction) but may be randomly oriented.

Figure 4A:
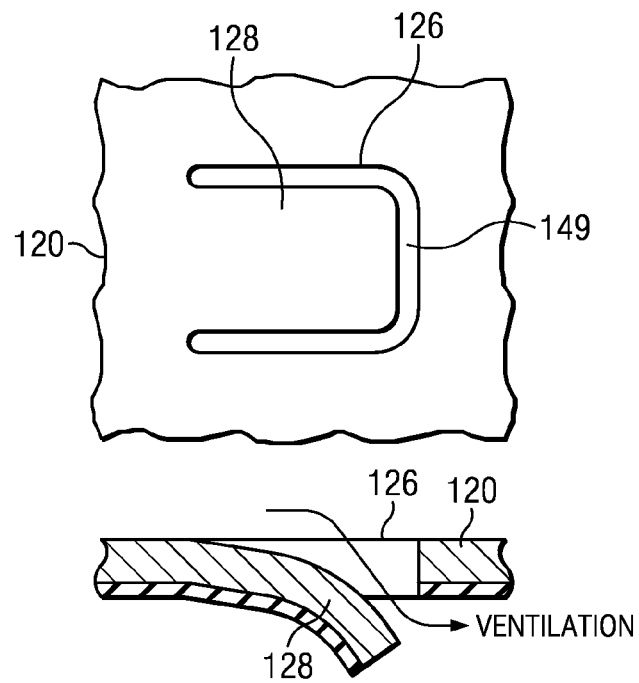
FIGS. 4a-e illustrate embodiments of layouts of a back-plate.

FIG. 4*a* shows a further embodiment of a layout of an opening location 126 in the back-plate 120. The opening location 126 is almost completely covered by the extension 128. There is only a small opening 149 forming a U. A layout with such a small opening 149 may still provide excellent ventilation because the extension 128 is bent and air still can circulate easily through the opening 149.

The layout of FIG. 4 may be used for applications that need minimum ventilation or high air damping. For example, the layout may be used for microphones for high sound pressure levels. In one embodiment the extension 128 may be relatively short and may bend less than the thickness of the back-plate 120.

Figure 4B:
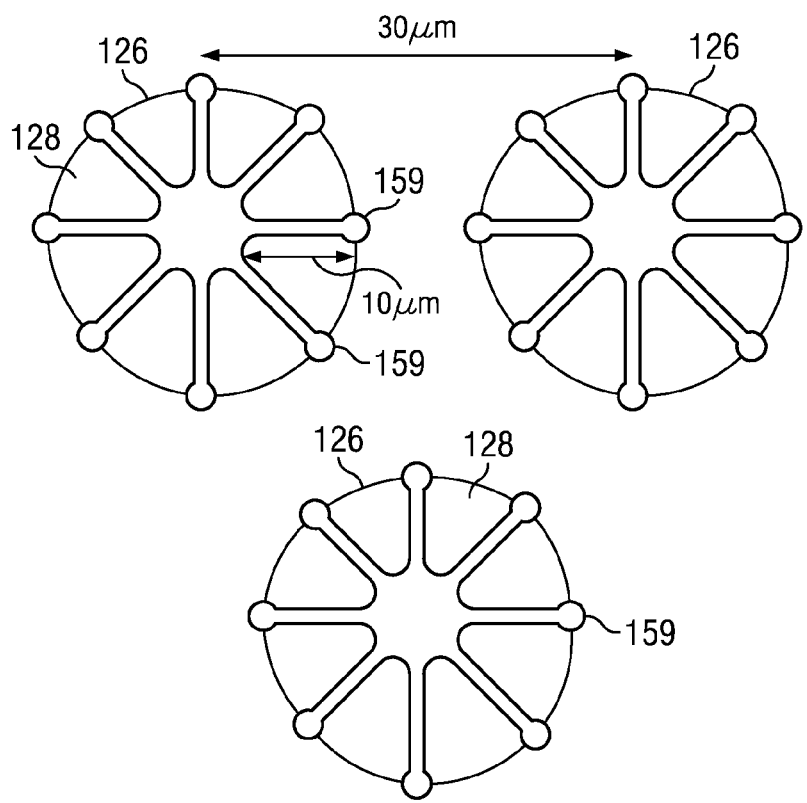

FIG. 4*b* shows another embodiment of a layout of opening locations 126 in the back-plate 120. A top view of the opening location 126 may comprise an opening 159 of a star. The area of the extensions 128 and the area of the opening 159 form the area of the opening location 126. In this example, eight extensions 128 shape the opening 159 forming the star. Each extension 128 may be a triangular cantilever with a round tip. The gap between two sides of two neighboring extensions 128 is 0.5 μm and the length of the gap is 10 μm. An effective open area of approximately 13% of the back-plate 120 is formed when the opening locations 126 are placed in a trigonal grid of 30 μm. Each of the eight extensions 128 may be bent away from the back-plate 120. In one embodiment the layout of FIG. 4 may be used in an application where large damping is desired.

Figure 4C:
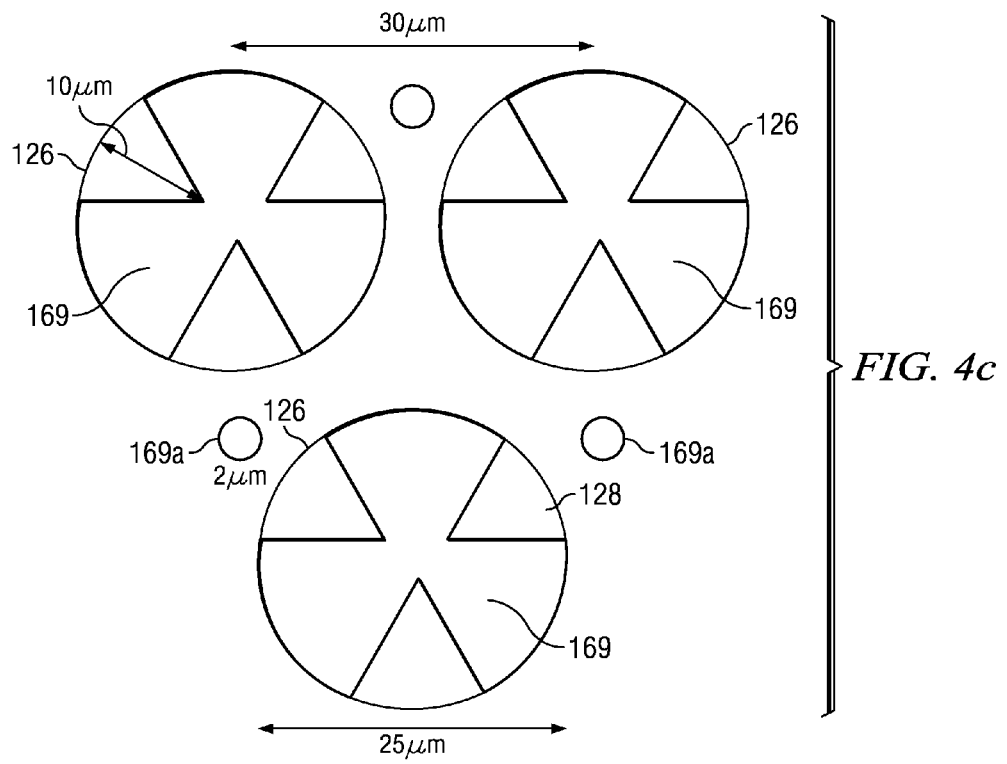

FIG. 4*c* shows another embodiment of a layout of an opening location 126 arrangement in the back-plate 120. A top view of the opening location 126 may comprise an opening 169 of a star. The area of the extensions 128 and the area of the opening 169 form the area of the opening location 126. Three extensions 128 shape the opening locations 126 forming the star opening 169. Each extension 128 may approximate a triangle with an angle tip. The length from the tip of the triangle to the circumferential line is 10 μm. The effective open area of openings 169 is approximately 37% of the overall back-plate 120 area when the opening locations 126 are placed in a trigonal grid of 30 μm. Compared to the situation shown in FIG. 4*b* this gives a much lower air damping since the opening 169 is much wider. Additional holes 169*a* between the opening locations 126 may reduce the release etching time of a sacrificial layer that is etched away when the membrane 130 and the back-plate 120 are formed.

Figures 4D, 4E:
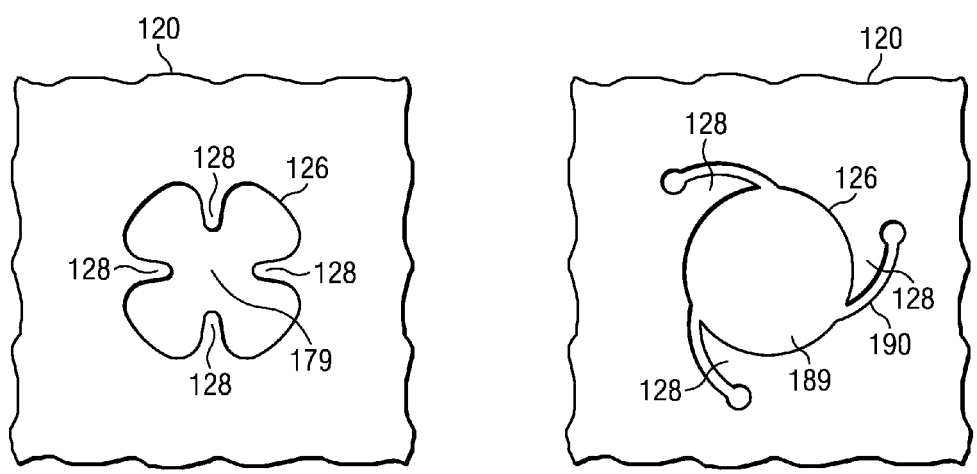

FIG. 4*d* shows another embodiment of a layout of an opening location 126 in the back-plate 120. The opening 179 of the opening location 126 has a form of a cloverleaf. The opening location 126 comprises four extensions 128 all with the same dimension. The extensions 128 form beams with round tips.

FIG. 4*e* shows yet another embodiment of a layout of an opening location 126 in the back-plate 120. The central aperture 189 forms a circle. Extensions 128 are created by cutting elongated aperture extension 190 into the back-plate material so that the extensions 128 form fins of a fish. The layout of FIG. 4*e* may be advantageous for layouts where there is less lateral space so that a spiral like design may help winding one or several extensions 128 around the central aperture 189.

For embodiments of opening locations 126 with more than one extension 128, the extensions 128 may all be bent, or alternatively, only some of the extensions 128 may be bent. Moreover, the number of extensions 128 for each of the embodiments of the opening locations shown in FIG. 4a-4e may vary between one and eight, for example.

The effective open area of openings in the back-plate 120 in FIGS. 3a-3d and 4a-4e depends on density of the placement of these opening locations relative to each other.

Figure 5:
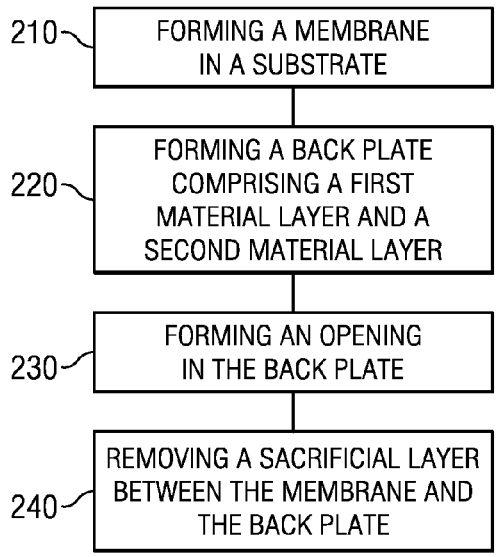
FIG. 5 illustrates a method for manufacturing a transducer.

FIG. 5 shows a method for manufacturing a transducer. In a first step 210 a membrane is formed in the support substrate. In a second step 220 a back-plate is formed. In one embodiment, the back-plate may be formed over the support substrate and the membrane. The back-plate may comprise a first material layer and a second material layer. The back-plate may be formed in a distance from the membrane. In one embodiment, an area between the back-plate and the membrane may be filled with a sacrificial layer and spacers.

In a third step 230, an opening is formed in the back-plate. An extension may extend into the opening. The extension and the opening may comprise an embodiment of a layout shown in FIGS. 3a-3d and 4a-4e. The opening may be formed by etching first the first material layer and then the second material layer. In one embodiment, the opening may be formed by two different etching steps using different etch chemistries. The form of the opening may be defined by a photoresist. After the etching of the opening is complete, a sacrificial layer may be removed between the membrane and the back-plate. This is shown in step 240. The sacrificial layer may be removed applying a wet-etch chemistry or a dry etch chemistry. The sacrificial layer may be removed through the opening and through additional holes also formed in the back-plate.

The extension of the opening may bend as soon as the opening is formed due to different stress properties of the first material layer and the second material layer.

The steps 210-240 in FIG. 5 may be performed in a different order than described in the previous paragraphs. For example, the sacrificial layer may be removed before the opening is formed.

Figure 6:
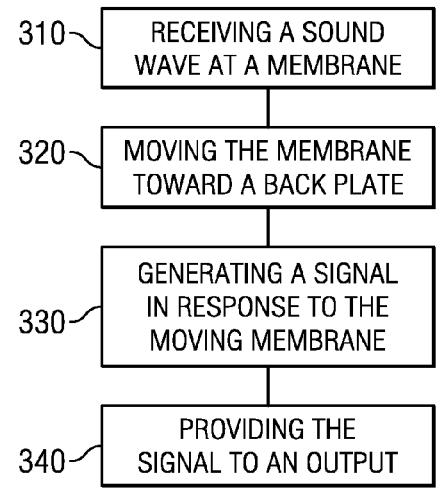
FIG. 6 illustrates a method for operating a transducer.

FIG. 6 shows a method for operating a transducer. In a first step 310 the method comprises receiving a sound wave at a membrane. In a second step 320 the membrane moves toward a back-plate. The back-plate may comprise an opening and an extension may shape the opening. The extension may be curved toward the membrane. The extension and the opening may comprise an embodiment of a layout shown in FIGS. 3a-3d and 4a-4e. In a third step 330 a signal is generated in response to the movement of the membrane. In one embodiment, in a fourth step 340 the signal may be provided to an output.

The procedures described in connection with FIGS. 5 and 6 may be realized utilizing the previously described implementations.

Figure 7:
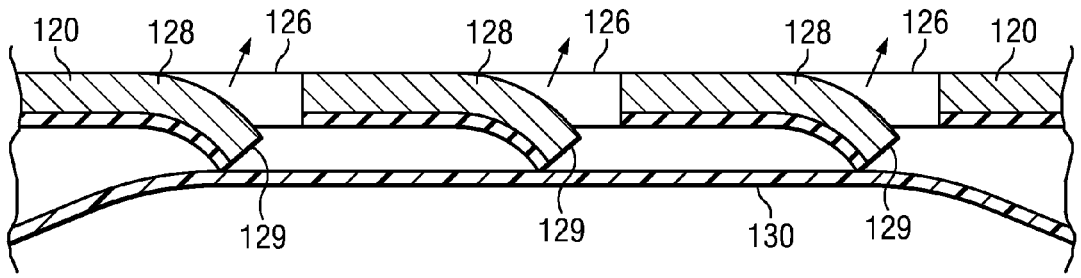
FIG. 7 illustrates a membrane pushing against the back-plate.

FIG. 7 shows an operational mode where the movable membrane 130 is pressed against the back-plate 120. Under normal operating conditions the membrane 130 may not touch the back-plate 120 or the bent extensions 128 of the back-plate 120. However, the operational mode of FIG. 7 may occur, for example, in the event of an over pressure, a huge static air pressure change, a shock or drop event, or an electrostatic over voltage causing a pull-in. The movable membrane 130 may be pressed first against the tips 129 of the extensions 128. At a certain predetermined pressure, the extensions 128 may yield to the pressing membrane 130. The extensions 128 may flatten, moving into their respective openings 199. Under extreme conditions, the extensions 128 may completely move into the openings 199 so that the top surfaces of the extensions 128 are coplanar with the top surface 121 of the back-plate 120. The extensions 128 may not pierce or destroy the membrane 130.

It is noted that the extensions 128 have a bending height h as described with regard to FIG. 2d. The bending height h may be the result of the two different stresses in the first and second material layers 122, 124 of the back-plate 120. The extensions 128 having the bending height h may be formed automatically or at the same time when the openings 199 are formed. The extensions 128 find an equilibrium height based on the stress combination in the back-plate 120. The extensions 128 may be temporarily displaced by exerting a force against them, e.g., when the membrane 130 presses against them. They may not break but rather yield relative to the pressing force. As soon as the force is removed the extensions return to their old equilibrium position.

Although the present invention and its advantages have been described in detail, it should be understood that various changes, substitutions and alterations can be made herein without departing from the spirit and scope of the invention as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A transducer device comprising:
a membrane; and
a backplate spaced apart from the membrane, the backplate comprising:
a first material layer comprising a first stress;
a second material layer arranged adjacent the first material layer, the second material layer comprising a second stress;
an opening extending through the first material layer and the second material layer; and
an extension shaping the opening, wherein the extension comprises a portion of the first material layer and a portion of the second material layer, and wherein the extension is curved towards the membrane.

2. The transducer according to claim 1, wherein the first material layer comprises a higher compressive stress than the second material layer.

3. The transducer according to claim 1, wherein the first material layer comprises a lower tensile stress than the second material layer.

4. The transducer according to claim 1, wherein the first material layer comprises a conductive material layer, and wherein the second material layer comprises an insulating material layer.

5. The transducer according to claim 1, wherein the first material layer comprises an insulating material layer and wherein the second material layer comprises a conductive material layer.

6. The transducer according to claim 1, wherein a deflection of the extension is larger than a thickness of the back-plate.

7. The transducer according to claim 1, wherein the extension comprises a cantilever.

8. The transducer according to claim 1, wherein the first material layer comprises a first conductive material layer and the second material layer comprises an insulating material layer, wherein the membrane comprises a second conductive material layer, and wherein the insulating material layer is arranged between the first conductive material layer of the backplate and the second conductive material layer of the membrane.

9. The transducer according to claim 8, wherein the first conductive material layer of the backplate is thicker than the insulating material layer of the backplate, wherein the first conductive material layer is between about 300 nm and about 3000 nm thick, and wherein the insulating material layer is between about 30 nm to about 300 nm thick.

10. The transducer according to claim 1, wherein the opening comprises a cloverleaf form.

11. The transducer according to claim 1, wherein the opening comprises a star form.

12. The transducer according to claim 1, wherein the opening comprises a spiral form.

13. A transducer device comprising:
a membrane; and
a backplate spaced apart from the membrane, the backplate comprising:
a first material layer comprising a first stress;
a second material layer arranged adjacent the first material layer, the second material layer comprising a second stress;
elongated openings extending through the first material layer and the second material layer; and
extensions shaping the elongated openings, wherein the extensions comprise portions of the first material layer and portions of the second material layer, and wherein the extensions are curved towards the membrane,
wherein the elongated openings are aligned such that first elongated openings are aligned in a first direction and second elongated openings are aligned in a second direction that is different from the first direction.

14. The transducer according to claim 13, wherein the first material layer comprises a lower tensile stress than the second material layer.

15. The transducer according to claim 13, wherein the first material layer comprises a higher compressive stress than the second material layer.

16. The transducer according to claim 13, wherein the elongated openings have single extensions.

17. The transducer according to claim 13, wherein deflections of the extensions are larger than a thickness of the backplate.

18. The transducer according to claim 13, wherein the first material layer comprises a first conductive material layer and the second material layer comprises an insulating material layer, wherein the membrane comprises a second conductive material layer, and wherein the insulating material layer is arranged between the first conductive material layer of the backplate and the second conductive material layer of the membrane.

19. The transducer according to claim 18, wherein the first conductive material layer of the backplate is thicker than the insulating material layer of the backplate, wherein the first conductive material layer is between about 300 nm and about 3000 nm thick, and wherein the insulating material layer is between about 30 nm to about 300 nm thick.

20. A transducer device comprising:
a membrane; and
a backplate spaced apart from the membrane, the backplate comprising:
a first material layer comprising a first stress;
a second material layer arranged adjacent the first material layer, the second material layer comprising a second stress;
elongated openings extending through the first material layer and the second material layer; and
extensions shaping the elongated openings, wherein the extensions comprise portions of the first material layer and portions of the second material layer, and wherein the extensions are curved towards the membrane,
wherein the elongated openings are symmetrically aligned such that first elongated openings are aligned in a first direction, second elongated openings are aligned in a second direction, third elongated openings are aligned in a third direction and fourth elongated openings are aligned in a fourth direction.

21. The transducer according to claim 20, wherein the first material layer comprises a lower tensile stress than the second material layer.

22. The transducer according to claim 20, wherein the first material layer comprises a higher compressive stress than the second material layer.

23. The transducer according to claim 20, wherein deflections of the extensions are larger than a thickness of the backplate.

24. The transducer according to claim 20, wherein the first material layer comprises a first conductive material layer and the second material layer comprises an insulating material layer, wherein the membrane comprises a second conductive material layer, and wherein the insulating material layer is arranged between the first conductive material layer of the backplate and the second conductive material layer of the membrane.

* * * * *